(12) United States Patent
Holberg et al.

(10) Patent No.: US 10,376,458 B2
(45) Date of Patent: Aug. 13, 2019

(54) METHODS OF REDUCING OR ELIMINATING TOOTH STAINING BY APPLICATION OF STAIN BARRIER FILMS

(71) Applicant: Hegemon Enterprises, LLC, Chester, NJ (US)

(72) Inventors: Walter Holberg, Apex, NC (US); Rhett M. Silverstein, New York, NY (US)

(73) Assignee: Hegemon Enterprises, LLC, Chester, NJ (US)

( * ) Notice: Subject to any disclaimer, the term of this patent is extended or adjusted under 35 U.S.C. 154(b) by 0 days.

(21) Appl. No.: 14/853,060

(22) Filed: Sep. 14, 2015

(65) Prior Publication Data

US 2016/0000684 A1    Jan. 7, 2016

Related U.S. Application Data

(63) Continuation of application No. PCT/US2014/027902, filed on Mar. 14, 2014.

(60) Provisional application No. 61/785,980, filed on Mar. 14, 2013.

(51) Int. Cl.
| | |
|---|---|
| *A61K 8/73* | (2006.01) |
| *A61Q 11/00* | (2006.01) |
| *A61K 8/365* | (2006.01) |
| *A61K 8/02* | (2006.01) |
| *A61K 8/25* | (2006.01) |

(52) U.S. Cl.
CPC ............ *A61K 8/732* (2013.01); *A61K 8/0204* (2013.01); *A61K 8/25* (2013.01); *A61K 8/365* (2013.01); *A61Q 11/00* (2013.01); *A61K 2800/92* (2013.01)

(58) Field of Classification Search
CPC ...... A61K 8/365; A61K 8/732; A61K 8/0204; A61K 8/25; A61K 2800/92; A61Q 11/00
See application file for complete search history.

(56) References Cited

U.S. PATENT DOCUMENTS

| | | | |
|---|---|---|---|
| 2002/0006386 A1 | 1/2002 | Ibsen et al. | |
| 2003/0211052 A1 | 11/2003 | Georgiades | |
| 2007/0190013 A1* | 8/2007 | Zhang ................... | A61K 9/006 424/70.13 |
| 2010/0240724 A1* | 9/2010 | Chang .................. | A61K 9/0056 514/394 |
| 2011/0008277 A1 | 1/2011 | Bruggerman et al. | |
| 2011/0065616 A1 | 3/2011 | Lourdin | |
| 2012/0048769 A1 | 3/2012 | Sivik et al. | |

OTHER PUBLICATIONS

Reddy et al., Food Chemistry, vol. 118, pp. 702-711, 2010.*

* cited by examiner

*Primary Examiner* — Lezah Roberts

(74) *Attorney, Agent, or Firm* — Calderone Bullock LLC

(57) ABSTRACT

The invention includes methods for reducing or preventing the staining capacity of a compound to a tooth in a mammalian oral cavity, which includes affixing to the tooth surface a degradable film. The film comprises a starch polymer or copolymer that is formed by crosslinking a starch. The film degrades in the oral cavity within about 1 minute to about 70 minutes after affixation. In some embodiments, it may be preferred the crosslinking occurs in the presence of at least one (poly)carboxylic acid. It may be preferred that the starch selected is a retrograde starch, a starch that is chemically or physically modified to be amylase resistant or a starch that is derived naturally but exhibits amylase resistance.

26 Claims, No Drawings

METHODS OF REDUCING OR ELIMINATING TOOTH STAINING BY APPLICATION OF STAIN BARRIER FILMS

CROSS REFERENCE TO RELATED APPLICATIONS

This application is a continuation of pending International Application Serial No. PCT/US2014/027902, filed Mar. 14, 2014 and entitled "Methods of Reducing or Eliminating Tooth Staining By Application of Stain Barrier Films," which in turn claims the benefit of priority under 35 U.S.C. § 119(e) to U.S. Provisional Patent Application No. 61/785,980, filed Mar. 14, 2013, entitled "Methods of Reducing or Eliminating Tooth Staining By Application of Stain Barrier Films", the entire disclosures of each of which are incorporated herein by this reference.

BACKGROUND OF THE INVENTION

Since the introduction of at-home tooth whitening kits, such as Crest "White Strips," and affordable professional dental whitening treatments in the early 2000s, a consumer subgroup of "whitening enthusiasts" has developed. Whitening enthusiasts generally utilize a both at-home whitening products and periodic professional whitening treatments to obtain a specific level of tooth visual whiteness. Such treatments are expensive and time consuming. At home tooth whiting kits can cost up to $500.00 and professional whitening treatments may cost significantly more. Moreover, both processes require significant treatment time.

However, even when the desired level of whiteness is obtained after expenditure of significant resources, it is difficult to maintain for long periods of time without inconvenience. Various ordinary habits can result in fairly rapid re-yellowing or staining of the teeth. In as little as a month, simple personal habits like the consumption of certain foods or drinks (e.g., coffee, tea, tomato sauce, red wine, cola, and chocolate) or smoking of cigars or cigarettes or chewing of tobacco can result in visually perceptible staining of the newly whitened teeth.

The whitening enthusiast is thus faced with an inconvenient choice: either forgo his/her personal habits or spend more time and money restoring his/her teeth to the desired whiteness level. Many are loathe to give up their morning cup of coffee or other treasured personal habit, and choose to repeat the whitening process, sometimes up to 3-4 times a month. In addition to being expensive, repeated whitening treatments result in increased tooth sensitivity, which may range from mildly uncomfortable to highly painful depending on the individual.

Accordingly, a need exists in the art for a device that can act as a temporary barrier between a tooth surface and a staining compound substantially preventing or reducing contact of the staining compound with the tooth surface, such that the substance contained in the staining compound (e.g., cigarette smoke or red wine) may be ingested by the whitening enthusiast in an ordinary manner. Additionally, it is desirable that the device is portable, not easily to visually discern when placed on the tooth surface, and removes in a convenient manner.

BRIEF SUMMARY OF THE INVENTION

The invention includes methods for reducing or preventing the staining capacity of a compound to a tooth in a mammalian oral cavity, which includes affixing to the tooth surface a degradable film. The film comprises a starch polymer or copolymer that is formed by crosslinking a starch. The film degrades in the oral cavity within about 1 minute to about 70 minutes after affixation. In some embodiments, it may be preferred the crosslinking occurs in the presence of at least one (poly)carboxylic acid. It may be preferred that the starch selected is a retrograde starch, a starch that is chemically or physically modified to be amylase resistant or a starch that is derived naturally but exhibits amylase resistance.

Also included within the scope of the invention are related films and kits.

DETAILED DESCRIPTION OF THE INVENTION

The invention described herein is directed to devices and methods that eliminate or reduce the ability of a staining compound to cause visually perceptible extrinsic and/or intrinsic staining or discoloration of a tooth. Such devices and methods are useful to individuals with natural colored teeth who wish to maintain the natural color, or to individuals who have invested time, money and other resources into the chemical whitening of their teeth. In addition, the invention includes methods of increasing the time span between a chemical tooth whitening treatment, as compared to the time span for those individuals who do not make use of the devices and/or methods of the invention.

The invention includes a device that is affixed to a surface of a tooth and which forms a barrier between the tooth and any materials that may include staining compounds. As used herein "tooth" is intended to include the hydroxyapatite ("HAP") tooth surface, the underlying (but often visible) dentin surface, and/or both surfaces. It is well settled in the art that staining of the HAP tooth surface is referred to using the shorthand "extrinsic" staining, while staining of the interior dentin is referred to as "intrinsic" staining. Such terms are used herein consistent with this meaning.

By "staining compound", it is meant any orally administered compound that is capable of altering the visually perceived color of the surface of a tooth via direct physical contact. Such color alteration my occur by any means at the molecular level—covalent bonding, lower energy bonding, hydrogen bonding, adherence via Van de Waals forces, etc. Common orally administered items that contain staining compounds include, for example, coffee, tea, chocolate, grape juice, red wine, tomato based products (sauce, juice), tobacco, and tobacco smoke.

The barrier films described herein serve to "reduce or prevent the staining capacity" of a given staining compound. This means that any staining to the tooth, extrinsic or intrinsic, attributable to contact with a staining compound is lessened or eliminated when the barrier is affixed, as compared to a tooth surface where the barrier was not affixed and the tooth was exposed to the staining compound under the same conditions.

The invention includes a film in a format that permits affixation to one or more teeth, such that the film provides coverage over at least a portion of the tooth. Such coverage may be continuous or discontinuous, although substantially continuous may be preferred. It may be preferred that the film is in a substantially rectangular format, such that it provides coverage for about 6 to about 8 or about 5 to about 10 adult teeth in situ (a "smile" span) in both the vertical and horizontal directions, optionally, with a small extra margin at the horizontal edge for foldover.

If desired in an embodiment, the format of the film may be modified or adapted to better fit or remain affixed to the teeth when in the oral cavity. Such modifications can include slits, perforations, rounded or curved corners or edges and the like. Exemplary formats include those disclosed in at least U.S. Pat. Nos. 6,514,483; 4,713,243; 6,096,328; and 5,879,691, the contents of each of which are incorporated herein by reference.

Similarly, the film may be of any thickness, and may be single or multiple layered. As will be recognized by a person of skill in the art, the thickness of a specific embodiment will depend on numerous factors, including amount of crosslinking of the starch, desired dissolution rate, surface area of the film, and the degree of structural integrity necessary in the film. For example, a film to be packaged on a reinforcing backing layer may be less robust than a film for which no backing layer is intended. As an example, in an embodiment, it may be preferred that the film has a thickness of about 20 to about 1500 micrometer ($\mu m$) or about 50 to about 1000 $\mu m$.

The film may be prepared by crosslinking a starch or a starch pre-copolymer. Any mechanism of cross linking known or to be developed in the chemical arts may be used. Preferably such crosslinking occurs in the presence of at least one mono or polycarboxylic acid. By "starch prepolymer" it is intended to mean copolymers that include a starch component linked to or polymerized with another, non-starch component or functional group. Any starch may be used independently for either the starch or the starch component of the starch pre-polymer.

Suitable starches include, without limitation, those derived from natural sources, such as banana, cassava, potato, corn, tapioca, arrowroot, wheat, rice, sorghum, yam, sweet potato, mango seed, rye, triticale, and barley starches. Synthetic starches, retrograde starches, and chemically or physically modified starches, may also be used, if desired. A single starch or a combination of two or more starches may be used.

The type(s) of starch selected for a given embodiment of the invention will vary depending on how long one wishes the barrier film to persist in the oral cavity. This is due to the fact that the dissolution rate of a barrier film may be varied depending on the chemical or physical structure of the starch, mixtures of starch and/or mixtures of starch(es) and starch additives selected. Without wishing to be bound by theory, it is surmised by the inventors that varying starch types (or combinations of starch(es) and additives) give rise to films of differing dissolution rates because of each individual starch's susceptibility to digestion by amylase and other hydrolytic enzymes present in saliva, which in turn is a function of the specific starch's chemical structure and/or the 'protective' function of a starch additive at the molecular level. If, for example, a relatively rapidly dissolving barrier film is desired (to be used, for example, during a quick coffee break), one may select corn starch, which results in a film that has a relatively fast rate of dissolution. Alternatively, if one wishes to have a barrier film that persists for 15-20 minutes, one may wish to formulate the film using, for example, a combination of a retrograded starch and a chemically modified starch, and/or a starch with a high level of amylopectin and low level of amylose.

In some embodiments, if may be desired that the starch is selected from the group consisting of those comprising amylose and amylopectin in a unit percentage ratio of about 0%:100%; about 10%:90%; about 20%:80%; 30%:70% and about 40%:60%. In other embodiments, the starch selected may have an amylose content of about 0 to about 39%. Further discussion of other potentially suitable starches is provided below.

It is well known in the art that starch is composed of linear (amylose) and branched (amylopectin) chains of glucose residues. In saliva, it undergoes gelatinization followed by amylase-induced hydrolysis. Amylose resistant starches have been both indentified in nature and developed by science. For example, starches containing lower levels of the amylose component and higher levels of the amylopectin component tend exhibit a higher degrees of crystallinity and to be more resistant to amylose digestion as compared to those containing higher amylose (e.g., 40% or greater) amounts. Alternatively, naturally occurring starches having structures that hinder amylase's access to the amylose component also exhibit varying degrees of resistance. Such starches may naturally occur in various plants, such as, for example, the raw, non-gelatinized starches derived from various types of banana or potato starch. It is known in the art that the resistance of these starches may be additionally enhanced by other processes, such as annealing or heat pre-treatments. See, for example, Leszczynski, Waclaw, *Resistant Starch—Classification, Structure, Production*, Pol. J. Food Nutr. Sci vol. 13/54, pp. 37-50; the contents of which are incorporated herein by reference. These amylose resistant starches may be suitable for use in the films and methods of the invention.

Starches having high amylose content can be retrograded or chemically modified to increase amylase resistance. Retrograded starches have also been found to be resistant to amylase as the retrograde process increases the crystallinity of the starch. Such starches may be suitable for use in the films and methods of the invention.

Various chemically modified starches exhibiting amylose resistance both known and to be developed in the art can also be used in the methods and films of the invention. These include, e.g., those prepared by the methods described in U.S. Pat. No. 5,593,503 and U.S. Patent Application Publication No. 2007/0183988, the contents of each of which are incorporated herein by reference. Others may include, for example, acetylated starches of papolionaceous plants or starches of papolionaceous plants that are modified by hydroxypropylation (the greater the substitution, the greater the resistance), acetylated distarch phosphoate, monostarch phosphate, phosphorylated resistant potato starch, and phosphorylated resistant corn starch.

Additionally, various physically modified starches may be suitable. These include starches containing starch additives that, it is believed, interact with portion of the starch molecule and reduce the rate of hydrolysis upon exposure to amylase. Examples may include starch/lipid mixtures, complexes of starch and monoglycerides of fatty acids, starches combined with any fatty acids. As used, herein, the term starch is intended to include starches that contain such starch additives.

In an embodiment, the selected starch or starches may be polymerized in the presence of a mono or a polycarboxylic acid.

Any mono- or polycarboxylic acid or mixture of mono- and/or polycarboxylic acids that is known or to be developed in the art may be used, provided that one or more acid(s) are selected compounds are relatively safe and non-toxic at the levels that may be released from the film under physiological conditions. Suitable monocarboxylic acids may include formic acid, acetic acid, butyric (butanoic) acid, propionic acid and valeric acid. As used herein, the term "polycarboxylic acid" is intended to include any compound(s) having two or more carboxy groups. The selected polycarboxylic acid may be added to the reaction as a pre-formed polycarboxylic acid or it may be delivered in the form of one or more precursor molecules, which, in the course of the selected reaction scheme, evolve to be polycarboxylic acid(s). For example, the precursor molecule may be one bearing a —C(OR)OH group, wherein the R group is removed in the course of the reactions, resulting in a —C(=O)OH-bearing intermediate compound.

In an embodiment, it may be preferred that the polycarboxylic acid is selected from one or more of oxalic acid, citric acid, formic acid, chloroacetic acid, dichloriacetic acid, trichloroacetic acid, trifluoroacetic acid, propionic acid, butyric acid, hydroxybutyric acid, valeric acid, caproic acid, glutaric acid. enanthic acid, caprylic acid, pelargonic acid, capric acid, undecylic acid, lauric acid, tridecylic acid, myristic acid, 1,2,3 propane tricarboxylic acid, nitrilacetic acid, ethylenediaminetetraacetic acid, ethyleneglycoltetraacetic acid acid, pentetic acid or diethylenetriaminepentaacetic acid, triethylenetetraminehexaacetic acid; 1, 2, 3, 4, butanetetracarboxylic acid, pentadecanoic acid, palmitic acid, margaric acid, stearic acid, arachidic acid, aldaric acid, isocitric acid, and tartaric acid. Others may include propandioic acid, butanedioic acid, pentaedioic acid, or any acid have the general formula $COOH(CH_2)_nCOOH$, where n may be selected from 0 or an integer of 1, 2, 3, 4, 5, 6, 7, and 8.

In an embodiment, it may be preferred that the polycarboxylic acid has at least 3, at least 4, at least 5 or at least 6 carboxy groups. For example, in an embodiment it may be preferred that citric acid is used, particularly if the embodiment is one in which it may be desired that the film affix relatively strongly to the tooth surface, in the absence of (or in addition to) an additional adherent. Without wishing to be bound by theory, it is hypothesized that in the process of crosslinking the starch, some of the carboxy groups on the citric acid may remain unreacted and form a citrate unit that attaches to the hydroxyapatite units present in tooth enamel. Cf., Misra, D. N. Interaction of Citric Acid with Hydroxyapatite: Surface Exchange of Ions and Precipitation of Calcium Citrate, JDR June 1996, 75:6 pp. 1418-1425.

It is believed that the starch and the polycarboxylic acid, when placed under suitable reaction conditions, will cross link mainly through the hydroxyl groups, as shown for example, in reaction Scheme 1 (where R represents a starch):

Scheme 1

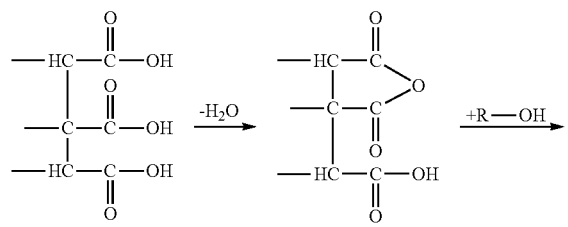

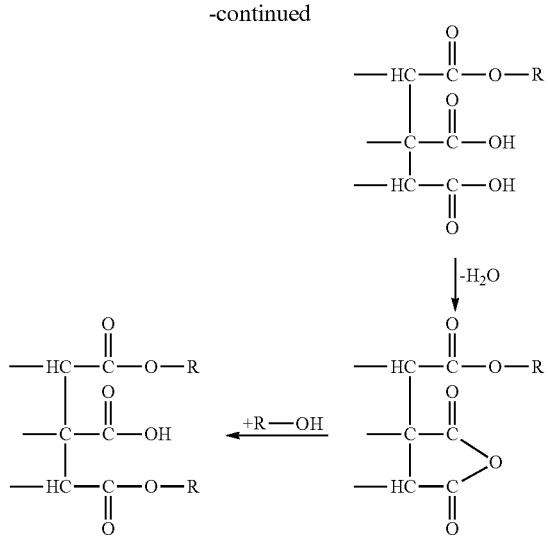

As an exemplary method to illustrate the polymerization of the starch and preparation the film, a starch or combination of starches is selected and dispersed in solvent, such as water. The amount of starch in the dispersion may vary depending on the specific end result desired. In an embodiment, the starch dispersion may be about 1% to about 7% (w/w), 3% top about 20%, or it may be preferred that it is about 2% to about 5% (w/w).

Additionally, in some embodiments, one may include other monomers or small polymers, so that, under suitable reaction conditions, the film will contain amount of other polymers or copolymers. For example, in an embodiment, one may add the monomers or polymers that result in the presence of one or more or acrylic polymers, cellulosic polymers, polyanhydride polymers, polyester polymers, polyacrylic acids, poly methyl methacrylates, PVO, PVA, and/or polyurethanes in the final film. The presence of these additional polymers may be used, for example, to adjust the physio-chemical properties of the film, for example, dissolution rate or tensile strength, as desired.

In may be preferred that these additional polymers are present in small amount relative to the starch. For example, about 1%-5% by weight as compared to the weight of starch present in the final film.

The dispersion may be heated, and processing aids or other additives (described below) may be added to the dispersion. A specified amount of citric acid and a catalyst (for example, sodium hypophosphite) is added to the starch dispersion. The amount of citric acid may be varied depending on the amount of crosslinking desired. For example, in an embodiment, the amount of citric acid may be about 20% to about 70% (w/w on weight of citric acid used); alternatively, it may be about 25, about 30%, about 35% about 40%, about 45%, about 50%, about 55%, about 60%, about 65% (each w/w on weight of citric acid used).

To form the films, the any standard film preparation process known or developed in the art may be used, for example, casting, rolling, spraying, conventional extrusion, calendaring, or pressing and the like. Once the film is prepared, it is desirable to dry the film, for example, either at ambient temperature or low heat. In most instances, the film is dried until substantially non tacky. Subsequently, the film may be allowed to cure under heat. Curing may be accomplished using may means known or to be developed in the art. Curing time and temperatures may be altered as is known in the art to facilitate the desired degree of cross-linking. For example, it may be desired to cure the film (1) at temperatures of about 90° C. to about 250° C., about 100° C. to about 200° C., or about 130° C. to about 170° C. and (2) over a duration of about 1 to about 60 minutes, about 10 to about 40 minutes, or about 25 or about 35 minutes.

Indeed, variations in the amount of cross linkages present in the film may also be achieved though routine modification of the reaction parameters, independently or in concert, including without limitation, cure temperature, duration of reaction and/or concentration of reagents.

In some embodiments, it may be preferred that the resultant film has a percent cross link average of about 0.1% to about 95%, bout 5% to about 80%, about 10% to about 85%, about 25% to about 75%, about 30% to about 65% or about 45% to about 60%. Alternatively, it may be desired that the percent cross linkage is about 0.01%, about 0.1%, about 0.3%, about 0.5%, about 0.7%, about 0.9%, about 1%, about 2%, about 3%, about 4%, about 5%, about 6%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, and about 40%.

In some embodiments, it may be desired that processing aids or texturizing agents or other components are included with the polymerization mixture so as to be included within the completed film. Such agents may include for example, plasticizers, glycerol, laponite, acrylic polymers, gelling agents such as, for example, carboxypoly-methylene, caroxymethyl cellulose, carboxyproyl cellulose, poloxamers, carrageenan, Veegum, caroxyvinyl polymers and natural gums such as gum karaya, xanthan gum, guar gum, gum Arabic, inulin, acrylate polymers, arcylate copolymers, polyvinylpyrrolidone, oils, waxes, and gum tragacanth. In some instances, these additives may also be used to adjust the dissolution time of the barrier film as well.

The starch film may contain other additives. Such additives may be any known or to be developed in the art and may include therapeutic or cosmetic, or aesthetic compounds. For example, one or more additives may be included in the polymerization mixture, so that the additives are present in the finished film. Alternatively or additionally, the additives may be delivered to the dried film in the form of a coating that may be, for example, sprayed or painted onto the film.

It may be desired in an embodiment that the starch film contains compounds capable of delivering a fluoride ion, for example, without limitation, sodium fluoride, potassium fluoride and/or ammonium fluoride, or an antimicrobial agent to promote gum health and fresh breath. Antimicrobial agents, may include, for example and without limitation, 5-chloro-2-(2,4-dichlorophenoxy)-phenol, phthalic acid and its salts, substituted monoperthalic acid and its salts and esters, magnesium monoperoxy phthalate, chlohexidine, alexidine, hexetidine, sanguinarine, bezalkonium chloride, salicylanilide, domiphen bromide, cetylpyridinium chloride (CPC), tertadecyl pridinium chloride (TPC), N-tetradecyl-4-ethylpyridinium chloride (TDEPC); octenidine; delmopinol, octapinol, nicin preparations, zinc/stannous ion agents, augmentin, amoxicilline, tetracycline, doxycylcine, monocycline, metronidazole, thymol, triclosan, geraniol, carvacrol, citral, hinokitiol, eucalyptol, catechol, 4-allyl catechol, methyl salicylate, hydrogen peroxide and metal salts of chlorite.

In an embodiment, one may wish to include with the film or to coat film with an anti-inflammatory agent, for example, ketorolac, flurbiprofen, ibuprofen, naproxen, indomethacin, aspirin, ketoprofen, piroxicam and meclofenamic acid.

Other additives that one may wish to include in various embodiments of the invention include, without limitation, antifungal agents, anticaries agents, colorants, flavorants, vitamins, silica nanoparticles, light scattering agents, fragrances, opacifiers, orally deliverable nutritional supplements, antioxidants, vitamin E, ascorbic acid, uric acid, carotenoids, vitamin A, flavonoids and polyphenols, herbal antioxidants, melatonin, aminoindoles, and lipoic acids.

In some embodiments, at least one side of the film is coated with an adhesive layer that serves to enhance the adherence of the film to a tooth surface. The adhesive layer may be continuous or discontinuous, and may be formed of any material known of to be developed in the art. In an embodiment, it may be preferred that the adhesive layer includes, for example, guar gum, xanthan gum, xylitol, granular starch, acrylic polymers, cellulose, laponite, smectite, carrageen, alginate, flour, locust bean gum, pectin, glycerol, or gelatin.

The film of the invention is capable of dissolving or degrading in the oral cavity under ordinary conditions. As will be understood to one of ordinary skill in the art, the rate of dissolution will vary depending on the structure and make up of the film—for example, film thickness, percent cross linkages and percent starch polymer (versus other polymers) may be altered to modify the dissolution rate.

In an embodiment, it may be preferred that the film is substantially completely degraded in the oral cavity in about 10 minutes to about 120 minutes, about 20 minutes to about 70 minutes, about 30 minutes to about 60 minutes after affixation to the tooth surface within the oral cavity. In some embodiments, the film may be substantially non-dissolvable under physiological conditions.

The film can be delivered to the consumer in any form. It may be packaged with a reinforcing backing sheet from which the consumer would peel the film before application, or it can be supplied without the backing sheet. Alternatively, and in the most basic iteration, the film can be packaged as large sheets, which the consumer can cut down to a size suitable for his or her needs. Alternatively, the film is provided to the consumer in a more convenient form—pre-cut or perforated into formats, with or without a backing layer, suitable for application to tooth surfaces. The film may be included in a dispensing device, for example: (i) a roll of film can be provided on a tape dispenser-like device, (2) several pre-cut films can be packaged in a box or pop-up dispensing device; (3) a small leaf of film with perforations can be provided in a flat, notebook-like device.

Example 1: Preparation of a Film for Use in the Method of the Invention

A mixture of commercially available corn starch and potato starch is prepared (1 part to 1 part by weight) and mixed thoroughly to ensure uniform dispersion of each of the starches. A starch dispersion is prepared by dispersing 3% (w/w) in water. To the dispersion, citric acid and the catalyst sodium hypophosphite (50% w/w, on weight of citric acid used) was added and agitation until dissolved. The starch dispersion is heated on a hot plate to 90° C. and held at that temperature for 20 min. The heated starch dispersion is cooled to about 65° C. and is poured onto Teflon-coated glass plates. The cast starch films air dry for about 48 hours before peeling them from the plates.

Example II: Evaluation of Barrier Functionality of Films of the Invention

A film of the invention was prepared by combining about 19.4 g of potato starch, 1.3 g of anhydrous citric acid, 0.3 g of sodium hypophosphite, 10 mL of glycerol and 120 g of water in a glass dish by through mixing to form a mixture. All components did not dissolve. The dish is placed on a room temperature hot plate and the hot plate is turned on. The contents of the dish are stirred constantly by hand with a silicone spatula and the temperature is monitored. When the mixture reaches about 80° C., it is observed that it changes from a milky white appearance to a substantially transparent appearance, which is considered to signify the initiation of polymerization.

Portions of the mixture are poured onto plastic sheeting about 20 minutes after transparency of the mixture was observed and dry under a stream of air. After drying, all films are easily removed from the plastic sheets. They are clear, colorless and very flexible. All were very strong, with resistance to sustained pulling and stretching.

10 hydroxyapetite disks of 5 inch diameter are affixed with the film of the invention as prepared above. 10 disks are left untreated. All of the disks are placed on a wire rack over a sink. 250 mls of brewed coffee (dark roast) is slowly poured over each disk and allowed to drain off the disk by gravity. This process is repeated for 500 times.

The relative whiteness of each of the disks is visually evaluated using a tooth color shade guide having colors 1 (whitest) to 55 (most stained), such as that shown in U.S. Pat. No. 4,978,296. On average, the control (untreated) disks exhibit a whiteness rating of about 32. The experimental (treated) disks exhibit a whiteness rating of about 21.

Example III: Use of Films to Prevent Tooth Staining

A whitening enthusiast and tea drinker, Individual A, using a tooth color shade guide having colors 1 (whitest) to 55 (most stained), such as that shown in U.S. Pat. No. 4,978,296, identifies her tooth shade as 4 by visual evaluation. For the next 30 days, she consumes between 2 and 5 cups of orange pekoe tea per day. At the end of the 30-day period, she evaluates her tooth shade and determines it to be about 7, possibly 8.

Individual A undergoes a series of professional whitening treatments. Upon completion of these treatments, she evaluates her tooth shade in the same manners and determines it to be about a 3. For the next 30 days, she consumes the same amount of tea on her 10 minute "tea break" (1 cup a day). However, each time, prior to consuming the tea, she applies a film of the invention (as prepared in Example I) to the surfaces of both her top and bottom teeth. The tea is consumed over a 3 minute period after which the films have dissolved so that Individual A does not have to manually remove them.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for reducing or preventing the staining capacity of a compound to a tooth in a mammalian oral cavity comprising affixing to the tooth surface a film that is pre-formed and that degrades upon exposure to amylase or hydrolytic enzymes within the oral cavity,
   wherein the film comprises a starch polymer or copolymer that is formed by crosslinking a starch or starch pre-copolymer, wherein the crosslinking occurs in the presence of at least one mono- or (poly)carboxylic acid, and
   wherein the film serves as a barrier that prevents staining of the tooth surface and degrades in the oral cavity within about 1 minute to about 70 minutes after affixation.

2. The method of claim 1, wherein the polycarboxylic acid is selected from the group consisting of oxalic acid, formic acid, chloroacetic acid, dichloriacetic acid, trichloroacetic acid, trifluoroacetic acid, propionic acid, butyric acid, valeric acid, caproic acid, enanthic acid, caprylic acid, pelargonic acid, capric acid, undecylic acid, lauric acid, tridecylic acid, myristic acid, pentadecanoic acid, palmitic acid, margaric acid, stearic acid, arachidic acid, aldaric acid, isocitric acid, and tartaric acid.

3. The method of claim 1, wherein the polycarboxylic acid is citric acid.

4. The method of claim 1, wherein the starch is selected from the group consisting of those comprising amylose and amylopectin in a unit percentage ratio of about 0%:100%; about 10%:90%; about 20%:80%; 30%:70% and about 40%:60%.

5. The method of claim 1, wherein the starch comprises about 100% amylopectin.

6. The method of claim 1, wherein the starch comprises an acetylated starch of papilionaceous plants, an acetylated distarch phosphate, and monostarch phosphate.

7. The method of claim 1, wherein the starch is extracted from a botanical source selected from corn, tapioca, arrowroot, wheat, rice, sorghum, yam, sweet potato, mango seed, rye, triticale, and barley.

8. The method of claim 1, wherein the starch is extracted from a botanical source selected from banana and potato.

9. The method of claim 1, wherein the wherein the film degrades in the oral cavity within about 10 minutes to about 60 minutes after affixation.

10. The method of claim 1, wherein the wherein the film degrades in the oral cavity within about 10 minutes or more.

11. The method of claim 1, wherein the film further comprises a member selected from the group consisting of inulin, an acrylate polymer, an acrylate copolymer, gum Arabic, an oil and a wax.

12. The method of claim 1, wherein the film further comprises at least one additional polymer, wherein the additional polymer is selected from the group consisting from acrylic polymers, cellulosic polymers, polyanhydride polymers, polyester polymers, polyacrylic acids, poly methyl methacrylates, and polyurethanes.

13. The method of claim 1, wherein the film further comprises a member selected from the group consisting of plasticizer, a flavorant, and a processing aid.

14. The method of claim 1, wherein the film is affixed to the tooth with an adhesive layer.

15. The method of claim 14, wherein the adhesive layer comprises a component selected from the group consisting of guar gum, xanthan gum, xylitol, granular starch, acrylic polymers, cellulose, laponite, smectite, carrageen, alginate, flour, locust bean gum, pectin, glycerol, and gelatin.

16. The method of claim 1, wherein the film further comprises sodium citrate.

17. The method of claim 1, wherein the film has a percent cross link average of about 5% to about 95%.

18. The method of claim 1, wherein the film has a percent cross link average of about 25% to about 75%.

19. The method of claim 1, wherein the film has a percent cross link average of about 45% to about 60%.

20. The method of claim 1, wherein the film further comprises a silica particle or nanoparticle.

21. The method of claim 1, wherein the film further comprises an additive.

22. The method of claim 21, wherein the additive is selected from the group consisting of anticaries agents, antibacterial agents, antisensitivity agents, fragrance, opacifiers, colorants, antifungal agents, and anti-inflammatory agents.

23. The method of claim 1, wherein the film further comprises a light scattering agent.

24. A method for reducing or preventing the staining capacity of a compound to a tooth in a mammalian oral cavity comprising affixing to the tooth surface a film that is pre-formed and that degrades upon exposure to amylase or hydrolytic enzymes in the oral cavity, wherein the film comprises a starch polymer or copolymer that is formed by crosslinking a starch or starch pre-copolymer in the presence of at least one (poly)carboxylic acid, and wherein the film serves as a barrier that prevents staining of the tooth surface and degrades in the oral cavity within about 1 minute to about 70 minutes after affixation.

25. A method for reducing or preventing the staining capacity of a compound to a tooth in a mammalian oral cavity comprising affixing to the tooth surface a film that is pre-formed and that degrades upon exposure to amylase or hydrolytic enzymes in the oral cavity, wherein the film comprises a starch polymer or copolymer that is formed by crosslinking a starch or starch pre-copolymer in the presence of at least one (poly)carboxylic acid, the starch comprising amylose and amylopectin in a unit percentage ratio of about 0%:100%; about 10%:90%; about 20%:80%; 30%:70% and about 40%:60%, wherein the film serves as a barrier that prevents staining of the tooth surface and degrades in the oral cavity within about 1 minute to about 70 minutes after affixation.

26. The method of claim 1, wherein the film degrades in the oral cavity within about 20 minutes to about 70 minutes after affixation.

* * * * *